(12) United States Patent
Declercq et al.

(10) Patent No.: US 9,040,056 B2
(45) Date of Patent: May 26, 2015

(54) METHODS AND COMPOSITIONS USEFUL FOR TREATING FITZPATRICK TYPE IV, V OR VI SKIN

(75) Inventors: Lieve Declercq, Ekeren (BE); Muriel Ghersin, Paris (FR); Louis De Saint Michel, Paris (FR); Joseph Scott Grigsby, New York, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 13/540,264

(22) Filed: Jul. 2, 2012

(65) Prior Publication Data

US 2013/0122036 A1 May 16, 2013

Related U.S. Application Data

(60) Provisional application No. 61/505,168, filed on Jul. 7, 2011.

(51) Int. Cl.
*A61K 8/97* (2006.01)
*A61K 8/891* (2006.01)
*A61Q 19/00* (2006.01)
*A61Q 1/02* (2006.01)

(52) U.S. Cl.
CPC ............ *A61K 8/975* (2013.01); *A61K 8/891* (2013.01); *A61K 8/97* (2013.01); *A61Q 19/007* (2013.01); *A61Q 19/008* (2013.01); *A61Q 1/02* (2013.01); *A61Q 19/00* (2013.01); *A61K 2800/28* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 6,982,284 B1 * | 1/2006 | Brown et al. ............... | 514/577 |
| 7,488,472 B2 | 2/2009 | Okuyama et al. | |
| 2006/0002884 A1 | 1/2006 | Golz-Berner et al. | |
| 2008/0119527 A1 * | 5/2008 | Baldo ......................... | 514/355 |
| 2009/0110650 A1 | 4/2009 | Candau | |
| 2010/0111893 A1 | 5/2010 | Mohammadi et al. | |
| 2010/0129465 A1 | 5/2010 | Blotsky et al. | |

FOREIGN PATENT DOCUMENTS

| | | |
|---|---|---|
| EP | 2140854 | 1/2010 |
| JP | 2005194277 | 7/2005 |
| JP | 2007-119430 | 5/2007 |
| JP | 2008195651 | 8/2008 |
| KR | 20080059818 | 7/2008 |
| WO | WO-03/013561 | 2/2003 |
| WO | WO2008/006739 | 1/2008 |
| WO | WO-2010043346 | 4/2010 |

OTHER PUBLICATIONS

Mar. 2011 http://web.archive.org/web/20110809045618/http://www.specialchem4cosmetics.com/services/inci/ingredient.aspx?id=12309.*
Sinha et al., Poly-ϵ-caprolactone microspheres and nanospheres: an overview, 2004, International J Pharmaceutics, 18: 1-23.*
http://www.gnpd.com; Mintel; Acne & Wrinkle Reducer; Record ID: 1278839; Murad; Murad Anti-Aging Acne; Skincare; Face/Neck Care; USA; Feb. 2020.
http://www.gnpd.com; Mintel; Anti-Aging Moisturizer SPF 20 PA++; Record ID: 1281439; Murad; Murad Anti-Agiing Acne; Skincare; Face/Neck Care; UK; Feb. 2010.
http://www.gnpd.com; Mintel; Double Corrector Acne Control; Record ID: 799406; L'Oreal; L'Oreal Dermo Expertise Pure Zone; Skincare; Face/Neck Care; Argentina; Oct. 2007.
http://www.gnpd.com; Mintel; Intensive Renewal Serum; Record ID: 1345665; Arbonne International; Arbonne RE9 Advanced; Skincare; Face/Neck Care; UK; Jun. 2010.
http://www.gnpd.com; Mintel; Velvety Coat Hand Cream; Record ID: 1437320; LG Household & Health Care; Bellf; Skincare; Hand/Nail Care; South Korea; Nov. 2010.
Muizzuddin, et al.; Structural and functional differences in barrier properties of African Amer, Caucasian and East Asian skin; J. of Derm. Sci; 59 Issue 2 (2010); pp. 123-128.
Estee Lauder; Idealist Pore Minimizing Skin Refinisher; Paula's Choice; XP002731114; Retrieved from the Internet: URL:http://www.paulaschoice.com/beautypedia-skin-care-reviews/by-brand/estee-lauder/idealist/_/Idealist-Pore-Minimizing-Skin-Refinisher; retrieved on Oct. 14, 2014.
Lee Hae Kwang, et al.; Phytocomponents of triterpenoids, oleanolic acid and ursolic acid, regulated differently the processing of epidermal keratinocytes via PPAR-alpha pathway; Experimental Dermatology; Jan. 2006; vol. 15, No. 1: pp. 66-73; XP002731115; ISSN: 0906-6705.
Supplemental European Search Report; EP12808235.1; Completion Date: Oct. 14, 2014; Mailing Date: Nov. 5, 2014.
PCT International Search Report; International Application No. PCT/US2012/044384; Completion Date: Jan. 31, 2013; Mailing Date: Feb. 1, 2013.
PCT Written Opinion of the International Searching Authority; International Application No. PCT/US2012/044384; Completion Date: Jan. 31, 2013; Mailing Date: Feb. 1, 2013.

* cited by examiner

*Primary Examiner* — Terry A McKelvey
*Assistant Examiner* — Catheryne Chen
(74) *Attorney, Agent, or Firm* — Julie Blackburn

(57) ABSTRACT

Compositions comprising a moisturizing agent, a desquamating agent, a mattifying agent and an agent that increases skin luminosity are disclosed herein. The compositions are useful for moisturizing, desquamating, mattifying, and increasing the luminosity in skin of an individual having a Fitzpatrick Skin Type IV, V, or VI. Also disclosed are methods for moisturizing, desquamating, mattifying, and increasing the luminosity in skin, comprising administering to an individual having a Fitzpatrick Skin Type IV, V, or VI, the present compositions.

11 Claims, 1 Drawing Sheet

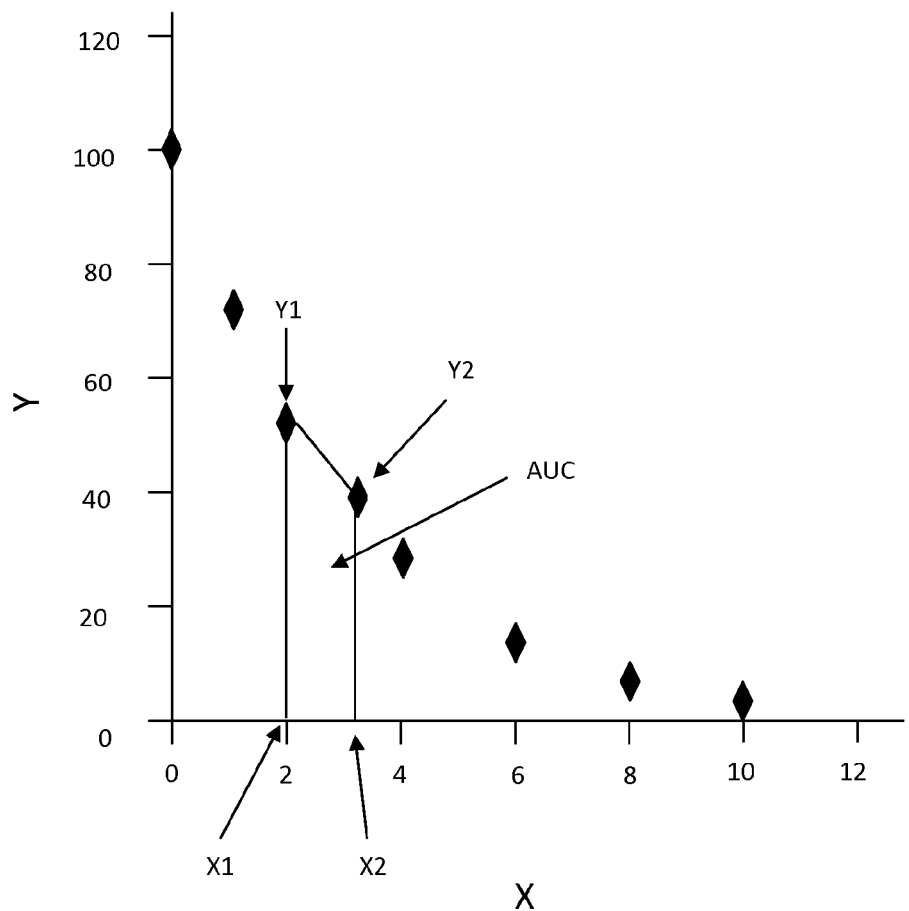

METHODS AND COMPOSITIONS USEFUL FOR TREATING FITZPATRICK TYPE IV, V OR VI SKIN

The present application claims priority from U.S. 61/505,168, filed Jul. 7, 2011.

TECHNICAL FIELD

The invention is in the field of skin care compositions useful for treating skin to, for example, improve moisturization, enhance desquamation, mattify, and increase skin luminosity.

BACKGROUND OF THE INVENTION

Dry skin is common among all skin types from very light-skinned individuals to, surprisingly, those individuals who have very dark skin that is often referred to as oily. The oily skin often found on darker skinned individuals (such as those having Fitzpatrick Type IV, V, and VI skin types) is generally caused by sebum, a mixture of lipids, waxes, and the debris of dead fat producing cells. While sebum was originally believed to be present for the purposes of lubricating skin, scientists have shown that that low levels of sebaceous gland activity do not correlate with dry skin. Downing D T, Stewart M E, Wertz P W, Colton S W, Abraham W, Strauss J S (March 1987). "Skin lipids: an update". *The Journal of Investigative Dermatology* 88 (3 Suppl): 2s-6s. The composition of sebum is generally believed to be about 25% wax monoesters, about 41% triglycerides, about 16% free fatty acids, and about 12% squalene.

It is now known that sebum does not lubricate or moisturize skin. Rather it tends to rest superficially on the skin surface and provide a shiny, oily appearance.

Ceramides, a family of lipid molecules found in high concentration in cell membranes of keratinocytes, are one component of the sphingomyelin lipids that make up the lipid bilayers of skin. As such ceramides are known to be excellent skin moisturizers. Interestingly enough, the keratinocytes of darker, oily skinned individuals tend to secrete an abundance of sebum but exhibit a deficiency of ceramides. This in turn causes the facial skin of these individuals to exhibit a shiny, oily appearance with underlying dry skin, and a generally dull, ashy skin tone and texture. The differences in skin properties of Caucasians, Blacks, and Asians are set forth in the article by Muizzuddin, et al., *Structural and Functional Differences in Barrier Properties of African American, Caucasian, and East Asian Skin, Journal of Dermatological Science*, Vol. 59 (2010): 123-128. Muizzudin, et al. demonstrate that African American subjects (those having Fitzpatrick Skin Types IV-VI) tend to exhibit a greater degree of skin scaliness, believed to be due to dryness caused by reduced ceramide levels in skin. Fitzpatrick skin types may be determined as set forth in Fitzpatrick, Thomas B.: *Soleil et Peau*. J Med Esthet 1975; 2:33034.

Cosmetics companies have developed products to treat each one of these conditions separately. For example, there are many well known products that contain different types of skin moisturizing agents including but not limited to ceramides. They are typically sold with marketing claims that they moisturize dry skin. Other types of products are known for desquamating skin (product marketing claims may refer to this as resurfacing), which is removing dead skin cells to provide smooth, fresh skin. Other types of products are sold for the purpose of reducing the oily shine on skin either by reducing sebum produced or absorbing sebum already produced which is referred to as "mattifying". Other products are sold with marketing claims that they improve skin luminosity or radiance. However, there are no single products that provide all the benefits of moisturization, desquamation, luminosity, and reducing the shiny appearance of oily skin by whatever mechanism (aka mattification), especially for darker skinned individuals who have oily but dry skin and are most likely to show a ceramide deficiency in the stratum corneum.

SUMMARY OF THE INVENTION

The invention relates to methods for moisturizing, desquamating, mattifying, and increasing the luminosity in skin, comprising administering to the skin of an individual having a Fitzpatrick Skin Type IV, V, or VI, and being in need of skin moisturization, desquamation, mattification or an increase in skin luminosity a composition comprising a moisturizing agent; a desquamating agent; a mattifying agent; and an agent that increases skin luminosity.

The invention also relates to methods for ameliorating an adverse effect of dry skin, comprising administering to the skin of an individual having Fitzpatrick Skin Type IV, V, or VI, and being in need of amelioration of an adverse effect of dry skin a composition comprising a moisturizing agent; a desquamating agent; a mattifying agent; and an agent that increases skin luminosity. Some of the adverse effects of dry skin that may be ameliorated include, but are not limited to, flaking, scaling, redness, itching, or cracking.

The invention also relates to methods for desquamating skin, comprising administering to the skin of an individual having Fitzpatrick Skin Type IV, V, or VI, and being in need of desquamation by administering a composition comprising a moisturizing agent; a desquamating agent; a mattifying agent; an agent that increases skin luminosity.

The invention also relates to methods for mattifying skin comprising administering to the skin of an individual having a Fitzpatrick Skin Types IV, V, or VI, and being in need of skin mattification a composition comprising a moisturizing agent; a desquamating agent; a mattifying agent; and an agent that increases skin luminosity.

The invention further relates to methods for increasing the luminosity of skin, comprising administering to an individual having a Fitzpatrick Skin Type IV, V, or VI and being in need of an increase in skin luminosity a composition comprising a moisturizing agent; a desquamating agent; a mattifying agent; and an agent that improves skin luminosity.

BRIEF DESCRIPTION OF THE FIGURE

The FIGURE is a plot of skin capacitance versus time after product application.

DETAILED DESCRIPTION

All percentages disclosed herein are percentages by weight unless otherwise indicated. All documents referred to herein are incorporated by reference in their entirety.

The word "about" when used in conjunction with an immediately following numeral means plus or minus 10% of the numeral. For example, "about 50%" means from 40% to 60%.

It is one object of the invention to provide a single multi-benefit composition that is useful to desquamate, moisturize, mattify, and provide luminosity to skin, especially to dark-skinned individuals who typically have Fitzpatrick IV, V, or VI skin types.

Most unexpectedly it has been shown that certain compositions will provide all of these benefits in one: desquamation, luminosity, moisturization, and mattification. Such compositions are especially effective in treating the skin of individuals with Fitzpatrick skin types IV, V, and VI.

It is another object of the invention to provide a method for moisturizing, desquamating, mattifying, and improving luminosity of Fitzpatrick Skin Types IV, V, or VI, comprising administering a single, multi-benefit composition to a dark-skinned individual.

The invention also relates to compositions comprising at least one moisturizer that enhances ceramide production in skin cells; at least one botanical desquamating agent; at least botanical mattifying agent; and at least one agent that enhances skin luminosity.

The Moisturizer

Suitable moisturizing agents useful in the compositions and methods of the invention include those which replenish ceramide on the skin surface or stimulate or enhance ceramide production in keratinocytes, specifically those found in facial skin, more specifically facial skin of individuals with Fitzpatrick skin types IV, V, or VI. The term "moisturize" or "moisturizer" refers to an agent that forms a film on skin that will enhance the ability of the skin to retain the moisture already present in the skin. The moisturizer may be present in the compositions in an amount ranging from about 0.0001 to about 30%, in another embodiment from about 0.001 to about 25%, and in another embodiment from about 0.005 to about 20%. Examples of moisturizing agents include Ceramide 1, 2, or 3; extracts of *Rosmarinus officinalis* including one or more of the components of *Rosmarinus officinalis* such as rosmarinic acid or ursolic acid; niacinamide; ascorbic acid and derivatives thereof such as esters of ascorbic acid and one or more fatty $C_{16-22}$ acids; hyaluronic acid; wheat germ; Barley extract; shea butter; and mixtures thereof.

The Desquamating Agent

Suitable desquamating agents useful in the compositions and methods of the invention include those which remove dead surface cells and debris from skin surfaces. The desquamating agent may be present in the compositions in an amount ranging from about 0.0001 to about 60%, in one embodiment from about 0.001 to about 50%, and in another embodiment from about 0.005 to about 30%. Suitable desquamating agents include agents that have inorganic or organic carboxylic acid functional groups, or esters thereof which may hydrolyze upon exposure to skin surfaces. Examples include alpha or beta hydroxy or keto acids; saccharide esters of $C_{2-10}$ carboxylic acids; or botanical extracts. Further specific examples include, but are not limited to acetyl glucosamine, *Castanea sativa* extract; salicylic acid; lactic acid; glycolic acid; maltobionic acid; gluconolactone; *Acacia senegal* gum; *Salix alba* (Willow) bark extract; yeast extract; glucono-heptono-lactone; D-mannose-6-phosphate salt, such as a sodium or potassium salt; polylysine; *Mucur miehei* (Mushroom) extract; galactoarabinan; lactobionic acid; L-serine lupin protein; salicin; sodium cholesterol sulfate; N-lactoyl phytosphingosine; forskolin; *Coleus barbatus* extract; lactic acid; Ceramide 6B (N(2-hydroxydecanoyl phytosphingsine)); Ceramide 6C(N(2-hydroxyoctanol) phytosphingosine)); phytic acid; cysteamine lactate; mandelic acid; hydroxylauric acid and mixtures thereof.

The Mattifying Agent

Suitable mattifying agents useful in the compositions and methods of the invention include those which reduce sebum production in keratinocytes or have sebum absorption properties. The mattifying agent may be present in the compositions in an amount ranging from about 0.0001 to about 60%, in one embodiment from about 0.001 to about 50%, and in another embodiment from about 0.005 to about 40%. Examples of mattifying agents include, but are not limited to silicone elastomers such as dimethicone crosspolymer, dimethicone/vinyl dimethicone crosspolymer; *Serenoa serrulata* (Saw Palmetto) fruit extract; *Laminaria saccharina* extract; NDGA (nordihydroguairetic acid); and mixtures thereof.

The Agent for Increasing Skin Luminosity

The compositions useful in the methods of the invention comprise an agent that improves skin luminosity. Useful ranges are from about 0.001 to about 30%, in one embodiment from about 0.005 to about 25%, and in another embodiment from about 0.01 to about 20% by weight of the total composition of such agent, which may be in the liquid, solid, or particulate solid form. Examples include silica, titanium dioxide either uncoated or coated with one or more of mica, silica, or mixtures thereof. Also suitable are polyvinyl alcohol crosspolymer and fluorescent brighteners such as those disclosed in U.S. Pat. No. 6,313,181. Examples include derivatives of stilbene and 4,4'-diaminostilbene such as bistriazinyl derivatives; derivatives of benzene and biphenyl or styryl derivatives; pyrazolines, bis(benzoxazol-2-yl) derivatives, coumarins, carbostyrils, naphthalimides, s-triazines, pyridotriazoles, and the like. A review of commonly used fluorescent brighteners that are also suitable as luminosity increasing agents may be found in "Fluorescent Whitening Agents", Kirk-Othmer Encyclopedia of Chemical Technology, Fourth Edition, Volume 11, Wiley and Sons, 1994, the contents of which are incorporated herein by reference.

The luminosity increasing agent may be an inorganic fluorescent glass, such as are described in U.S. Pat. Nos. 5,635, 109, and 5,755,998, the contents of which are incorporated herein by reference. More specifically, this type of glass may be any type of fluorophosphate containing fluorescent glass exhibiting a visible fluorescence, or a Tb- or Eu-containing fluorophosphate containing fluorescent glass capable of converting invisible ultraviolet rays into visually observable visible rays. A wide variety of such compounds are available commercially from, for example, Keystone Aniline Corporation, Ciba Specialty Chemicals, and Sumita Optical Glass, Inc.

In one embodiment compounds sold by Ciba-Geigy corporation under the Tinopal trademark may be suitable. Such ingredients include Tinopal 5BM having the chemical name diaminostilbene disulfonic acid; Tinopal BG which is a mixture of butylene glycol and disodium distyrylbenzenesulfonate; Tinopal CBS-X which is disodium distyrylbenzenesulfonate; Tinopal solution which is a mixture of water and disodium distyrylbenzenesulfonate.

In another embodiment, the brightener may be a fluorescent glass, such as Lumilass G9 sold by Sumita.

In another embodiment the brightener may be one sold by Keystone Aniline under the Keyfluor trademark, which is a 2,2'-(2,5 thiophene diyl)bis(5-tert-butylbenzoxazole).

In another embodiment the luminosity inorganic fluorescent glass, Lumilass B from Sumita. Other fluorescence categories include red or orange, as represented, for example by Lumilass R7. In one preferred embodiment, the material is selected from those emitting blue or green fluorescence, or combinations thereof, so as to directly mimic the skin's natural fluorescent color. However, in another embodiment, the ingredient's fluorescent color can be any one or a combination of colors, the selection being made for the purpose of enhancing, complementing, or counteracting a given skin tone color. These brighteners may include those sold by Lipo Chemicals Inc. under the trademark LipoLite OAP/PVA having the C.T.F.A. name polydodeanamideaminium Triazadiphenylethenesulfate. Also suitable are particulates such as mica, boron nitride, nylon-12, nylon-6, and HDI/PPG-polycaprolactone crosspolymer (e.g. hexamethylene diisocyante/polypropylene glycol-polycarpolactone crosspolymer), including those particulates having a particle size ranging from about 0.05 to 150 microns. In one embodiment the skin luminosity increasing agent is silica, optionally in combination with a multi-layer pigment comprised of layers of titanium dioxide/mica/silica.

Other Ingredients

The moisturizing, desquamating, mattifying, and skin luminosity agents may be incorporated into a wide variety of cosmetic compositions that are in the liquid, solid, or semi-solid form. The compositions may be anhydrous, or in the aqueous emulsion or solution form. If in emulsion form, the composition may be a water-in-oil or oil-in-water emulsion. Such emulsions typically comprise from about 0.1 to about 95%, in one embodiment from about 1 to about 80%, in another embodiment from about 5 to about 75% water and from about 0.1 to about 95%, in another embodiment from about 0.1 to about 80% and in another embodiment from about 1 to about 75% oil. The compositions useful in the methods of the invention may be in the form of skin creams, lotions, serums, foundation makeup, blush, lipstick, concealer, and sprays.

Humectants

The compositions useful in the methods of the invention may optionally comprise one or more humectants. If present, the humectant is present in an amount of from about 0.01 to about 25%, in one embodiment from about 0.05 to about 20%, in another embodiment from about 1 to about 15% by weight of the composition. Examples of humectants include mono-, di-, or polyhydric alcohols such as glycerin, propanediol, or C2-5 alkylene glycols such as propylene glycol, butylene glycol, ethylhexyl glycerin, sodium pyroglutamate, sodium pyrrolidone carboxylic acid, urea, trehalose, hyaluronic acid or a salt thereof including sodium hyaluronate, or pentylene glycol. In one embodiment the humectant is glycerin, ethylhexyl glycerin or mixtures thereof.

Oils

The compositions used in the methods of the invention may optionally comprise one or more oils. Oils may be in the form of silicones, hydrocarbons, glucosides, glutamates, or esters such as glyceryl esters of fatty acids. In one embodiment the oil is a volatile or non-volatile hydrocarbon. The term "volatile" means that the hydrocarbon has a vapor pressure of greater than about 2 mm of mercury at 20° C. The term "non-volatile" means that the hydrocarbon has a vapor pressure of less than 2 mm of mercury at 20° C.

Cyclic silicones are one type of volatile silicone that may be used in the composition. Such silicones have the general formula:

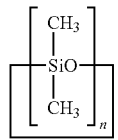

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the trade names Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

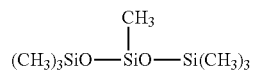

Methyl trimethicone may be purchased from Shin-Etsu Silicones under the tradename TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, or polymeric olefins which may or may not be hydrogenated such as polyisobutene, hydrogenated polyisobutene, polydecene, hydrogenated polydecene, mineral oil, pentahydrosqualene, squalene, squalane, and mixtures thereof.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Examples of glucosides include the reaction product of glucose and $C_{12-22}$ fatty acids such as cetearyl glucoside, stearyl glucoside, and the like.

Examples of esters include mono-, di-, or triesters of glycerol and $C_{16-22}$ fatty acids such as caprylic or capric triglycerides, tridecyl trimellitate, bis-behenyl/isostearyl/phytosteryl dimer dilinoleate and mixtures thereof.

Examples of glutamates include phytosteryl/octyldodecyl lauroyl glutamate which is glutamic acid esterified with phytosteryl alcohol and octyldodecyl alcohol.

Microcirculation Enhancer

The compositions useful in the methods of the invention may optionally comprise a microcirculation enhancer that promotes increased blood flow in facial skin. If present the microcirculation enhancer may range from about 0.00001 to about 10% by weight of the composition. Examples of suitable microcirculation enhancers include *Gingko biloba* extract, caffeine, *Acmella oleracea* extract of which spilanthes is the active ingredient, and the like.

Other Botanical Extracts

The compositions useful in the methods of the invention may also optionally comprise a botanical extract for providing further desirable properties such as anti-inflammatory activity, antioxidant activity, anti-allergenic activity, and the like. If present the botanical extracts may range from about 0.0001 to about 20%, in one embodiment from about 0.005 to about 15%, in another embodiment from about 0.01 to about 10% by weight of the composition. Examples include extracts of fruits, seeds, flowers, roots, leaves, such as *Santalulm album* (Sandalwood) extract, *Phellodendron amurense* bark extract, *Hordeum distichon* (Barley) extract, *Rosmarinus officinalis* (Rosemary) extract, *Laminaria saccharina* extract and *Citri reticulate* peel extract.

Viscosity Increasing Agents

The compositions useful in the methods of the invention may optionally comprise a viscosity-increasing agent. If present, the viscosity-increasing agent ranges are from about 0.001 to about 35%, in one embodiment from about 0.005 to about 30%, and in another embodiment from about 0.01 to about 25% by weight of the composition. The viscosity-increasing agents may be water-soluble or oil-soluble.

Polysaccharides may be suitable viscosity-increasing agents. Examples of such polysaccharides include naturally derived polysaccharides such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose and gelatin.

Other suitable viscosity-increasing agents are polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof. In one embodiment the A monomer comprises one or more of acrylic acid or methacrylic acid, and the B monomer is selected from the group consisting of a $C_{1-10}$, in one embodiment $C_{1-4}$ alkyl acrylate, a $C_{1-10}$, in one embodiment $C_{1-4}$ alkyl methacrylate, and mixtures thereof. In other embodiments the B monomer is one or more of methyl acrylate, ethyl acrylate and methacrylate. The acrylic copolymer may be present in an aqueous solution having a solids content ranging from about 10 to about 60%, in one embodiment from about 20 to about 50%, in another embodiment from about 25 to about 45% by weight of the polymer, with the remainder being water. The composition of the acrylic copolymer may comprise from about 0.1 to about 99 parts of the A monomer, and about 0.1 to about 99 parts of the B monomer. Useful acrylic polymer solutions include those sold by Seppic, Inc., under the tradename Capigel.

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate-based polymers where one or more of the acrylic groups optionally has one or more substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Other suitable viscosity-Increasing agents are acrylate-based polymeric thickeners sold by Clariant under the Aristoflex trademark such as Aristoflex AVC, which is ammonium acryloyldimethyltaurate/VP copolymer; Aristoflex AVL which is ammonium acryloyldimethyltaurate/VP copolymer dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

Various types of polyethylene glycols (PEG) derivatives where the degree of polymerization ranges from 1,000 to 200,000 are also useful as viscosity-increasing agents. Such ingredients are indicated by the designation "PEG" followed by the degree of polymerization in thousands as designated by "M," such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable as viscosity-increasing agents are polyglycerins which are repeating glycerin moieties where the number of repeating moieties ranges from about 15 to about 200, in one embodiment from about 20 to about 100. Examples of suitable polyglycerins include those having the CFTA names polyglycerin-20, polyglycerin-40, and the like.

In other embodiments the viscosity-increasing agents are acryloyl dimethyl taurate copolymers such as ammonium/acryloyldimethyltaurate/VP copolymer and acrylates C10-30 alkyl acrylate crosspolymer where "VP" means vinyl pyrrolidone.

Surfactants

The compositions of the invention can optionally comprise a surfactant, particularly when the compositions are in emulsion form. When present, the surfactant ranges from about 0.001 to about 30%, in one embodiment from about 0.005 to about 25%, and in another embodiment from about 0.01 to about 20% by weight of the composition.

Examples of nonionic surfactants include alkoxylated alcohols, or ethers, obtainable by the reaction of an alcohol with an alkylene oxide, such as ethylene or propylene oxide. In one embodiment the alcohol is a fatty alcohol having 6 to 30 carbon atoms. Examples of such nonionic surfactacts include Steareth 2-100, which is obtainable by the reaction of stearyl alcohol and ethylene oxide, where the number of ethylene oxide units ranges from 2 to 100; Beheneth 5-30, which is obtainable by the reaction of behenyl alcohol and ethylene oxide, where the number of repeating ethylene oxide units is 5 to 30; Ceteareth 2-100, obtainable by the reaction of cetyl and stearyl alcohol with ethylene oxide, where the number of repeating ethylene oxide units in the molecule is 2 to 100; and Ceteth 1-45, which is obtainable by the reaction of cetyl alcohol and ethylene oxide, where the number of repeating ethylene oxide units is 1 to 45.

Other alkoxylated alcohols that are useful as nonionic surfactants are obtainable by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000. In this case less than all of the available hydroxyl groups of a di- or polyhydric alcohol react with the carboxylic acid, and the remaining hydroxyl groups (or less than all of them) react with an alkylene oxide.

Also suitable as nonionic surfactants are those obtainable by the reaction of a carboxylic acid with an alkylene oxide or with a polymeric ether. The resulting nonionic-surfactant products have the general formula:

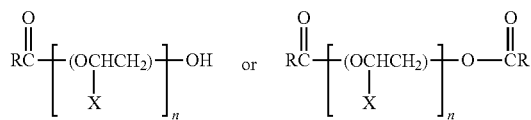

where RCO is the fatty acid acyl group, X is hydrogen or lower alkyl, and n is the number of polymerized alkoxy groups. In the case of the diesters, the two RCO-groups do not need to be identical. In one embodiment, R is a $C_{6-30}$ straight or branched chain, saturated or unsaturated alkyl, and n is from 1 to about 100.

Monomeric, homopolymeric, or block copolymeric ethers are also suitable as nonionic surfactants. Typically, such ethers are obtainable by the polymerization of monomeric alkylene oxides, such as ethylene or propylene oxide. Such polymeric ethers have the following general formula:

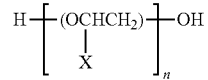

wherein X is H or lower alkyl and n is the number of repeating monomer units, and ranges from 1 to about 500.

Other suitable nonionic surfactants include alkoxylated sorbitan and alkoxylated sorbitan derivatives. For example, alkoxylation, in particular ethoxylation of sorbitan, provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, in one embodiment $C_{12-22}$ fatty acids. Examples of such sorbitan-related nonionic surfactants include Polysorbates 20-85 where the designation "20-85" refers to the number of repeat units, sorbitan oleate, sorbitan sesquioleate, sorbitan palmitate, sorbitan sesquiisostearate, and sorbitan stearate.

In one embodiment, the moisturizer wheat germ extract. In another embodiment the moisturizing agent is Barley extract. In yet another embodiment the moisturizing agent is *Rosmarinus* extract.

In another embodiment, the luminosity-increasing agent is HDI/PPG/-polycaprolactone crosspolymer or titanium dioxide/mica/silica. In another embodiment, the mattifying agent is *Serenoa serrulata* or *Laminaria saccharina* extract. In another embodiment, the desquamating agent is *Castenea sativa* extract or *Salix alba* extract.

In another embodiment the moisturizer is wheat germ, the luminosity-increasing agent is HDI/PPG/-polycaprolactone crosspolymer, the mattifying agent is *Serenoa serrulata* and the desquamating agent is *Castenea sativa* extract.

In another embodiment the moisturizer is wheat germ, the luminosity-increasing agent is HDI/PPG/-polycaprolactone crosspolymer, the mattifying agent is *Serenoa serrulata* and the desquamating agent is *Salix alba* extract.

In another embodiment the moisturizer is wheat germ, the luminosity-increasing agent is HDI/PPG/-polycaprolactone crosspolymer, the mattifying agent is *Laminaria saccharina* and the desquamating agent is *Castenea sativa* extract.

In another embodiment the moisturizer is wheat germ, the luminosity-increasing agent is HDI/PPG/-polycaprolactone crosspolymer, the mattifying agent is *Laminaria saccharina* and the desquamating agent is *Salix alba* extract.

The invention will be described in connection with the following Examples which are set forth for the purposes of illustration only.

EXAMPLE 1

Assignment of the Fitzpatrick Skin Type scores IV-VI is made by using the following method.

Phenotype Disposition

| Score | 0 | 1 | 2 | 3 | 4 |
|---|---|---|---|---|---|
| What is the color of your eyes? | Light blue, grey, green | Blue, grey or green | Blue | Dark brown | Brownish black |
| What is the natural color of your hair? | Sandy red | Blond | Chestnut/dark blond | Dark brown | Black |

-continued

| Score | 0 | 1 | 2 | 3 | 4 |
|---|---|---|---|---|---|
| What is the color of your skin on non-exposed areas? | Reddish | Very pale | Pale with beige tint | Light brown | Dark brown |
| Do you have freckles on unexposed areas? | Many | Several | Few | Incidental | None |

Total Score for Genetic Disposition: _____

Reaction to Sun Exposure

| Score | 0 | 1 | 2 | 3 | 4 |
|---|---|---|---|---|---|
| What happens when you stay in the sun too long? | Painful redness, blistering, peeling | Blistering followed by peeling | Burns, sometimes followed by peeling | Rare burns | Never had burns |
| To what degree do you turn brown? | Hardly or not at all | Light color tan | Reasonable tan | Tan very easily | Turn dark brown quickly |
| Do you turn brown within several hours after sun exposure? | Never | Seldom | Sometimes | Often | Always |
| How does your face react to the sun? | Very sensitive | Sensitive | Normal | Very resistant | Never had a problem |

Total Score for Reaction to Sun Exposure: _____

Tanning Habits

| Score | 0 | 1 | 2 | 3 | 4 |
|---|---|---|---|---|---|
| When did you last expose your body to sun (or artificial sunlamp/tanning cream)? | More than 3 months ago | 2-3 months ago | 1-2 months ago | Less than 1 month ago | Less than 2 weeks ago |
| Did you expose the area to be treated to the sun? | Never | Hardly ever | Sometimes | Often | Always |

Total Score for Tanning Habits: _____

Add up the total scores for each of the three sections to determine Fitzpatrick Skin Type Score:

| Score | Skin Type |
|---|---|
| 0-7 | I |
| 8-16 | II |
| 17-25 | III |
| 25-30 | IV |
| Over 30 | V-VI |

Type I: highly sensitive, always burns, never tans. Example is red hair with freckles.

Type II: very sun sensitive, burns easily, tans minimally. Example is fair skinned, fair haired Caucasians.

Type III: Sun sensitive skin, sometimes burns, slowly tans to light brown. Example is darker skinned Caucasians.

Type IV: Minimally sun sensitive, burns minimally, always tans to moderate brown. Example is Mediterranean-type Caucasians.

Type V: Sun insensitive skin, rarely burns, tans well. Example is some Hispanics, some blacks.

Type VI: Sun insensitive skin, never burns, deeply pigmented. Example is darker blacks.

EXAMPLE 2

Compositions in accordance with the invention were prepared as follows:

| Ingredient | % by weight | |
|---|---|---|
| Water | QS100 | QS100 |
| Glycerine | 3.00 | 3.75 |
| Caprylic/capric triglyceride | 3.00 | 3.00 |
| Hydrogenated polyisobutene | 2.00 | 2.00 |
| Cetearyl alcohol/cetearyl glucoside | 2.00 | 2.50 |
| Propanediol | 2.00 | 2.00 |
| Tridecyl trimellitate | 1.50 | 1.50 |
| *Santalum album* (sandalwood) extract/ *Phellodendron amurense* bark extract/ *Hordeum distichon* (Barley) extract (20:20:60) | 1.50 | |
| *Phellodendron amurense* bark extract/ *Hordeum distichon* (Barley) extract | | 1.50 |
| Water/*Castanea sativa* (Chestnut) seed extract (90:10) | 1.00 | 1.00 |
| Isododecane/hydrogenated polydecene/bis-behenyl/isostearyl/phytosteryl dimer dilinoleyl dimer dilinoleate (64:34:2) | 1.00 | |
| Neopentyl glycol diethylhexanoate | | 1.00 |
| Water/ergothioneine | 1.00 | 1.00 |

| Ingredient | % by weight | |
|---|---|---|
| Potassium palmiotyl hydrolyzed wheat protein/glyceryl stearate/cetearyl alcohol | | 0.50 |
| Water/lecithin/*Rosmarinus officinalis* (Rosemary) leaf extract (98:0.5:0.5) | 1.00 | 0.75 |
| Water/butylene glycol/*Laminaria saccharina* extract (68:31:1) | 1.00 | 1.00 |
| Glycerin/water/sodium PCA/urea/trehalose/polyquaternium-51/sodium hyaluronate (34:11:0.5:1:10:40.4:1 | 1.00 | 2.00 |
| HDI/PPG/polycaprolactone crosspolymer/silica (98:2) | 0.7 | 0.70 |
| Ammonium acryloyl dimethyltaurate/VP copolymer | 0.60 | 0.80 |
| Phenoxyethanol | 0.60 | 0.50 |
| Methyl gluceth-20 | 0.50 | 0.50 |
| Betaine | 0.50 | 0.50 |
| *Butyrospermum parkii* (Shea butter) | 0.50 | 0.50 |
| Steareth-21 | 0.50 | |
| Ethylhexylglycerin | 0.30 | 0.30 |
| Acrylates/C10-30 alkyl acrylate crosspolymer | 0.30 | 0.30 |
| Phytosteryl/octyldodecyl lauroyl glutamate | 0.25 | 0.25 |
| Titanium dioxide/mica/silica | 0.25 | 0.25 |
| Cholesterol | 0.20 | 0.20 |
| Silica | 0.20 | 0.20 |
| Squalane/*Hordeum vulgare* (Barley) extract/*Triticum vulgare* (Wheat) germ extract (75:15:10) | | 0.20 |
| Butylene glycol | | 0.13 |
| Salicylic acid/*Acacia senegal* gum | 0.20 | 0.15 |
| Disodium EDTA | 0.10 | 0.05 |
| Tocopheryl acetate | 0.10 | 0.10 |
| Sodium hydroxide | 0.10 | 0.08 |
| Water/alcohol/*Salix alba* (Willow) bark extract (60:30:1) | 0.10 | 0.10 |
| Hyaluronic acid | 0.10 | 0.10 |
| Tetrahexyldecyl ascorbate | 0.10 | 0.10 |
| Caffeine | 0.10 | 0.20 |
| Potassium sorbate | 0.05 | 0.05 |
| *Ginkgo biloba* leaf extract | 0.05 | 0.05 |
| Butyl avocadate | | 0.05 |
| *Serenoa serrulata* (Saw palmetto) fruit extract | 0.05 | |
| *Citri reticulatae* peel extract | 0.01 | 0.01 |

EXAMPLE 3

The following compositions A, B, C, and D were prepared with the parenthetical number after each letter referring to an internal designation:

| Ingredient | % by weight | | | | |
|---|---|---|---|---|---|
| | A (11) | B (12) | C(39) | D(43) | E(3) |
| Water | QS100 | QS100 | QS100 | QS100 | QS100 |
| Glycerin | 4.00 | 4.00 | 4.00 | 4.00 | 2.00 |
| Hydrogenated polydecene | 4.00 | 2.00 | — | — | — |
| Caprylic/capric triglyceride | 3.00 | | 3.00 | 3.00 | |
| Hydrogenated polyisobutene | 2.00 | 1.00 | 2.00 | 2.00 | |
| Cetearyl alcohol/cetearyl glucoside | 2.00 | 1.00 | 2.50 | 2.50 | |
| Tridecyl trimellitate | 1.50 | 0.75 | 1.50 | 1.50 | |
| Acetyl glucosamine | 1.00 | 1.00 | | | |
| Glycerin/water/sodium PCA/urea/trehalose/Polyquaternium-51/sodium hyaluronate | 1.00 | 1.00 | 2.00 | 2.00 | |
| Water/butylene glycol/*Laminaria digitata* extract | 1.00 | 1.00 | 1.00 | 1.00 | |
| Isododecane/hydrogenated polydecene/bisbehenyl/isostearyl/phytostearyl dimer dilinoleyl dimer dilinoleate | 1.00 | 1.00 | 1.00 | 1.00 | |
| Water/lecithin/*Rosmarinus officinalis* (Rosemary) leaf extract (98:0.5:0.5) | 1.00 | 1.00 | 1.00 | 1.00 | |
| Water/arginine/salicylic acid/tocopheryl acetate/mixed soya phospholipids | 1.00 | 1.00 | | | |
| Propylene glycol dicaprate/*Helianthus annus*/*Hordem vulgare*/*Cucumis sativus* extract | | | | | |
| Potassium sorbate | | | 0.05 | 0.05 | |
| Dimethicone | | | 0.0011 | 0.0011 | |
| Cyclopentasiloxane | | | | 0.500 | |
| Cyclopentasiloxane/dimethicone | | | | | 4.00 |
| Declustered water | | | | | 3.00 |
| Trehalose | | | | | 1.00 |
| Hydroxyethyl urea | | | | | 1.00 |
| Sucrose | | | | | 1.00 |
| Phenoxyethanol | | | | | 0.60 |
| Sorbitol | | | | | 0.50 |
| Tromethamine | | | | | 0.30 |
| Carbomer | | | | | 0.30 |
| Butylene glycol | | | 0.133 | 0.133 | 4.50 |
| Hydrogenated lecithin | | | | | 0.20 |
| Caprylyl glycol/phenoxyethanol | | | | | 0.15 |
| Glyceryl polymethacrylate/PEG-8 | | | | | 0.10 |
| Sodium hyaluronate | | | | | 0.10 |
| Magnesium ascorbyl phosphate | | | | | 0.01 |

-continued

| Ingredient | A (11) | B (12) | C(39) | D(43) | E(3) |
|---|---|---|---|---|---|
| Oleth-10 | | | | | 0.30 |
| *Camellia sinensis* leaf extract | | | | | 0.01 |
| Lady's thistle (*Silybum marianum*) extract | | | | | 0.01 |
| *Thermus thermophillus* ferment/glycerin | | | | | 0.01 |
| Sodium hyaluronate | | | | | 0.01 |
| Phenoxyethanol | 0.61 | 0.61 | 0.60 | 0.60 | 0.09 |
| Ammonium acryloyldimethyl taurate copolymer | 0.60 | 0.60 | 0.80 | 0.80 | 1.00 |
| Methyl gluceth-20 | 0.50 | 0.50 | 0.50 | 0.50 | |
| Betaine | 0.50 | 0.25 | 0.50 | 0.50 | |
| Potassium palmitoyl hydrolyzed wheat protein/glyceryl stearate/cetearyl alcohol | 0.50 | 0.25 | 0.50 | 0.50 | |
| *Butyrospermum parkii* (Shea butter) | 0.50 | 0.25 | 0.50 | 0.50 | |
| Acrylates C10-30 alkyl acrylate crosspolymer | 0.30 | 0.30 | 0.30 | 0.30 | |
| Phytosteryl/octyldodecyl lauroyl glutamate | 0.25 | 0.25 | 0.25 | 0.25 | |
| Titanium dioxide/Mica/Silica | 0.25 | | 0.25 | 0.25 | |
| Cholesterol | 0.20 | 0.20 | 0.20 | 0.20 | |
| Silica | 0.20 | 0.20 | 0.20 | 0.20 | |
| Sodium benzoate | 0.15 | 0.15 | | | |
| Disodium EDTA | 0.10 | 0.10 | 0.10 | 0.10 | 0.15 |
| Tocopheryl acetate | 0.10 | 0.10 | 0.10 | 0.10 | |
| Sodium hydroxide | 0.10 | 0.10 | 0.09 | 0.09 | |
| Caffeine | 0.10 | 0.10 | 0.20 | 0.20 | 0.20 |
| Tetrahexyldecyl ascorbate | 0.10 | 0.10 | 0.10 | 0.10 | |
| Water/alcohol/*Salix alba* (Willow) bark extract | 0.10 | 0.10 | 0.10 | 0.10 | |
| Hyaluronic acid | 0.10 | 0.10 | 0.10 | 0.10 | |
| *Serenoa serrulata* (Saw Palmetto) fruit extract | 0.05 | 0.05 | 0.05 | 0.05 | |
| *Ginkgo biloba* leaf extract | 0.05 | 0.05 | 0.05 | 0.05 | |
| *Citri reticulatae* peel extract | 0.01 | 0.01 | 0.01 | 0.01 | |
| Sodium chloride | 0.008 | 0.008 | | | |
| Disodium phosphate | 0.001 | 0.001 | | | |
| Ergothioneine | 0.0005 | 0.0005 | | | |
| Potassium phosphate | 0.0002 | 0.0002 | | | |
| Potassium chloride | 0.0002 | 0.0002 | | | |
| *Santalulm album* (Sandalwood) extract | | 1.50 | 1.50 | 1.50 | |
| Mica/titanium dioxide | | 0.25 | | | |
| Propanediol | | | 2.00 | 2.00 | |
| HDI/PPG/Polycaprolactone crosspolymer | 0.70 | 0.70 | 0.70 | 0.70 | |
| Water/*Castanea sativa* (Chestnut) seed extract (90:10) | | | 1.00 | 1.00 | |
| Water/ergothioneine | | | 1.00 | 1.00 | |
| Ethylhexylglycerin | | | 0.30 | 0.30 | |
| Salicylic acid/*acacia senegal* gum | | | 0.20 | 0.20 | |
| Squalane/*Hordeum vulgare* extract/*Triticum vulgare* (wheat) germ extract | | | 0.20 | 0.20 | |

Formulas A-D are illustrative compositions of the invention. Formula E is a reference formula, which was used as a comparative example.

Two commercial, prestige cosmetic compositions, Formulas F and G were purchased. Formula F is Clarins Gel Crème Fraicheur Désaltérant Super Hydratant (peaux normales á mixtes ou Climats chauds). The ingredient list on Formula F reads as follows:

Aqua, glycerin, caprylic/capric triglyceride, pentylene glycol, cetearyl isononanoate, tapioca starch, hydroxyethyl acrylate/sodium acryloyldimethyltaurate copolymer, acrylates/C10-30 alkyl acrylate corsspolymer, parfum, ethylhexylglycerin, PPG-5 ceteth-20, tocopheryl acetate, tromethamine, alcohol, butylenes glycol, glyceryl acrylate/acrylic acid copolymer, phenoxyethanol, mica, titanium dioxide, *Cedrelopsis Grevei* bark extract, *pyrus sorbus* bud extract, biosaccharide gum-4, sodium hyaluronate, *thermos thermophillus* ferment, methylisothiazolinone, *Epilobium fleischeri* exract, *Lapsana commnis* flower/leaf/stem extract, *Punica granatum* bark extract, triethoxycaprylylsilane, *Camellia sinensis* leaf extract, potassium sorbate, *Rhodiola rosea* root extract, sodium lauryl sulfate, Yellow 6.

Formula G is Dior Crème Sorbet Hydra Life. The ingredient listing for Formula G reads as follows:

Aqua, Isononyl isononanoate, glycerin, caprylic/capric triglyceride, pentylene glycol, phenyl trimethicone, butylene glycol, steareth-2, betaine, alcohol, steareth-21, phenoxyethanol, polymethylmethacrylate, cetyl alcohol, stearyl alcohol, decyloxazolidinone, rose hybrid flower extract, ammonium acryloyldimethyltaurate/VP copolymer, dimethicone, acrylates/C10-30 alkyl acrylate crosspolymer, tetrasodium EDTA, tocopheryl acetate, polyacrylamide, C13-14 isoparaffin, *Centella asiatica* leaf extract, dimethicone/phenyl vinyl dimethicone crosspolymer, parfum, sodium hydroxide, *Malva sylvestris* (Mallow) extract, laureth-7, hydrolyzed *Opuntia ficus*-indica flower extract, hyaluronic acid, sodium aluronate, ethylhexylglycerin, *Ajuga turkestanica* extract, BHT.

Two clinical studies were performed. In Study I, Formulas A, B, and E, F, and G were tested. In Study II, Formulas C, D, E, F, and G were tested.

For both Study I and Study II a minimum of ten subjects having a mean age of 48 years with minimum age 23 and maximum age 74 having a Fitzpatrick Skin Type II or III participated. On the volar forearm of each subject, 4×8 centimeter sites were marked with a maximum of 3 sites on each arm. One site was reserved for Formula E (the reference formula). The skin capacitance of each area was measured at the start of the study using a Corneometer® CM825 with a Multi Probe Adapter MPA5 and associated software MPA5 (Courage & Khazaka). The button "Corneometer" on the instrument was selected. The probe was placed perpendicularly on the skin surface. The measurements, expressed in corneometer units (which are representative for the hydration of the skin) appeared on the screen. The measurement was performed at least 5 times on different sites in close vicinity to each other. The measurement was repeated until the standard deviation of the last 5 measurements was smaller than 2. One hundred microliters (3 μL/cm$^2$) of the formulations was applied to the designated sites. The skin capacitance at each site was measured at 30 minutes, 3 hours and 6 hours after Formula application using the Corneometer® and method set forth above. The skin capacitance values measured at the start of the experiment (before Formula application) were subtracted from the values measured at 30 minutes, 1 hour, 3 hours, and 6 hours after Formula application. The baseline-corrected capacitance values were plotted as a function of time. The area under the curve was then calculated. Integrated areas and baseline-corrected skin capacitance values were expressed relative to the reference formulation using the equations below:

$$\text{Relative integrated area (\%)} = \frac{\text{total area under the curve(Formula } X)}{\text{Total area under the curve (Formula } E)}$$

$$\text{Relative hydration level (\%)} = \frac{\text{skin capacitance at 6 hours (Formula } X)}{\text{skin capacitance at 6 hours (Formula } E)}$$

where Formula X is Formula A, B, C, D, F or G. The values obtained above are plotted with the time after product application in hours on the X axis and the baseline corrected capacitance on the Y axis. Each line segment forms a trapezoid, and its area is calculated with the following equation: $(X2-X1)\times(Y2+Y1)/2$, for example, as graphically depicted in the FIGURE. The total area under the curve is calculated by adding all of the calculated areas for each time interval measured. The "relative integrated area" as calculated above, is used to determine relative hydration capacity compared to a reference formula that is tested alongside test samples. The following results were obtained:

| | Formula | | | | | | |
|---|---|---|---|---|---|---|---|
| | A | B | C | D | E | F | G |
| Relative Hydration Level - 6 Hours - % | 149 | 168 | 159 | 162 | 100 | 133 | 141 |

| | Formula | | | | | | |
|---|---|---|---|---|---|---|---|
| | A | B | C | D | E | F | G |
| Relative Integrated Area % | 119 | 135 | 159 | 156 | 100 | 118 | 138 |

The above results demonstrate that the compositions of the invention exhibit superior hydration at 6 hours for all skin types when compared to the reference Formula (E) and, in most cases, when compared to Formulas F and G.

EXAMPLE 4

Clinical studies were performed on 25 subjects of Afro-Caribbean or African descent having Fitzpatrick Skin Type V or VI and ranging in age from 24 to 46 years of age. The panelists were provided with the following Formula H:

| Ingredient | % by weight |
|---|---|
| Water | QS100 |
| Glycerin | 3.75 |
| Caprylic/capric triglyceride | 3.00 |
| Hydrogenated polyisobutene | 2.00 |
| Propanediol | 2.00 |
| Glycerin/water/sodium PCA/urea/trehalose/polyquaternium-51/sodium hyaluronate | 2.00 |
| Tridecyl trimellitate | 1.50 |
| *Phellodendrom amurense* bark extract/*hordeum distichon* (barley) extract | 1.50 |
| Cetearyl alcohol/cetearyl glucoside | 1.25 |
| Neopentyl glycol diethylhexanoate | 1.00 |
| Ammonium acryloyldimethyltaurate/VP copolymer | 1.00 |
| Water/butylene glycol/*Laminaria saccharina* extract | 1.00 |
| Water/ergothioneine | 1.00 |
| Water/*Castanea sativa* (Chestnut) seed extract | 1.00 |
| Water/lecithin/*Rosmarinus officinalis* (Rosemary) leaf extract | 0.75 |
| HDI/PPG/Polycaprolactone crosspolymer/silica | 0.70 |
| Methyl gluceth-20 | 0.50 |
| *Butyrospermum parkii* (Shea butter) | 0.50 |
| Phenoxyethanol | 0.50 |
| Betaine | 0.50 |
| Ethylhexylglycerin | 0.30 |
| Acrylates/C10-30 alkyl acrylate crosspolymer | 0.30 |
| Phytosteryl/octyldodecyl lauroyl glutamate | 0.25 |
| Potassium palmitoyl hydrolyzed wheat protein/glyceryl stearate/cetearyl alcohol | 0.25 |
| Titanium dioxide/mica/silica | 0.25 |
| Caffeine | 0.20 |
| Silica | 0.20 |
| Squalane/*Hordeum vulgare* (Barley) extract/*Triticum vulgare* (Wheat) germ extract | 0.20 |
| Squalane/*Hordeum vulgare* extract/*Triticum vulgare* (wheat) germ extract | |
| Cholesterol | 0.20 |
| Salicylic acid/*Acacia senegal* gum | 0.15 |
| Butylene glycol | 0.133 |
| Tocopheryl acetate | 0.10 |
| Tetrahexyldecyl ascorbate | 0.10 |
| Water/alcohol/*Salix alba* (Willow) bark extract | 0.10 |
| Hyaluronic acid | 0.10 |
| Sodium hydroxide | 0.08 |
| Disodium EDTA | 0.05 |
| *Ginkgo biloba* leaf extract | 0.05 |
| Butyl avocadate | 0.05 |
| Potassium sorbate | 0.05 |
| *Citri reticulatae* peel extract | 0.01 |
| FD&C Yellow 5 | 0.002 |
| FD&C Yellow 6 | 0.001 |

Panelists were given a sample of the Formula H and asked to apply it to their facial skin. The immediate effect and the effect two hours after application were assessed for mositurization, hydration, luminosity, mattification, desquamation and oil-breakthrough control. In addition, panelists self-assessed of how well Formula H moisturized and hydrated their skin. Moisturizers are considered to be agents that have an occlusive effect when applied to skin and thereby enhance the ability of the skin to retain water already present. A hydrating agent is generally an agent that adds water back to the skin.

Moisturization:

| Grade | Immediately after Application (# panelists showing the effect) | After 2 hours (# panelists showing the effect) | Total: |
|---|---|---|---|
| Extremely Effective | 3 | 2 | 5 |
| Very Effective | 10 | 12 | 22 |
| Somewhat Effective | 7 | 6 | 13 |
| Total: | 20 | 20 | — |

Panelist Self-Assessment of Moisturized Feel to Skin:

| Grade | Immediately after Application (# panelists showing the effect) | After 2 hours (# panelists showing the effect) | Total: |
|---|---|---|---|
| Extremely Effective | 2 | 3 | 5 |
| Very Effective | 7 | 10 | 17 |
| Somewhat Effective | 9 | 4 | 13 |
| Slightly | 1 | 3 | 4 |
| Total: | 19 | 20 | — |

Hydration:

| Grade | Immediately after Application (# panelists showing the effect) | After 2 hours (# panelists showing the effect) | Total: |
|---|---|---|---|
| Extremely Effective | 3 | 1 | 4 |
| Very Effective | 8 | 8 | 16 |
| Somewhat Effective | 4 | 9 | 13 |
| Slightly Effective | 4 | 2 | 6 |
| Total: | 19 | 20 | — |

Panelist Self-Assessment of Hydrated Feel to Skin:

| Grade | Immediately after Application (# panelists showing the effect) | After 2 hours (# panelists showing the effect) | Total: |
|---|---|---|---|
| Extremely Effective | 2 | 3 | 5 |
| Very Effective | 3 | 3 | 6 |
| Somewhat Effective | 10 | 13 | 23 |
| Slightly | 4 | 1 | 5 |
| Total: | 19 | 20 | — |

Skin Luminosity:

| Grade | Immediately after Application (# panelists showing the effect) | After 2 hours (# panelists showing the effect) | Total: |
|---|---|---|---|
| Extremely Effective | 2 | 2 | 4 |
| Very Effective | 8 | 8 | 16 |
| Somewhat Effective | 9 | 8 | 17 |
| Slightly Effective | 1 | 2 | 3 |
| Total: | 20 | 20 | — |

Mattified Skin:

| Grade | Immediately after Application (# panelists showing the effect) | After 2 hours (# panelists showing the effect) | Total: |
|---|---|---|---|
| Extremely Effective | 2 | 3 | 5 |
| Very Effective | 6 | 7 | 13 |
| Somewhat Effective | 9 | 8 | 17 |
| Slightly Effective | 2 | 2 | 4 |
| Total: | 19 | 20 | — |

Soft/Smooth Skin (Desquamation):

| Grade | Immediately after Application (# panelists showing the effect) | After 2 hours (# panelists showing the effect) | Total: |
|---|---|---|---|
| Extremely Effective | 3 | 2 | 5 |
| Very Effective | 9 | 10 | 19 |
| Somewhat Effective | 3 | 5 | 8 |
| Slightly Effective | 4 | 3 | 7 |
| Total: | 19 | 20 | — |

Controlling Oil Breakthrough During Day:

| Grade | Immediately after Application (# panelists showing the effect) | After 2 hours (# panelists showing the effect) | Total: |
|---|---|---|---|
| Extremely Effective | NA | 2 | 2 |
| Very Effective | NA | 6 | 6 |
| Somewhat Effective | NA | 9 | 9 |
| Slightly Effective | NA | 2 | 2 |
| Total: | NA | 19 | — |

NA = not available

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claim is:

1. A method of treating skin of an individual with Fitzpatrick Skin Type IV, V, or VI having: (i) dry skin due to deficient ceramide production; (ii) dead cells and debris on skin surface; (iii) skin that has an oily, shiny appearance due to excessive sebum production; and (iv) an ashy, chalky skin tone comprising administering to the skin of a person having Fitzpatrick Skin Type IV, V, or VI a composition comprising effective amounts of (a) a moisturizing agent that replenishes ceramide on the skin surface and/or enhances ceramide production in skin cells selected from the group consisting of Ceramide 1, Ceramide 2, Ceramide 3, *Rosmarinus officinalis* extract, rosmarinic acid, ursolic acid, ascorbic acid, esters of ascorbic acid, wheat germ, barley extract, shea butter, and mixtures thereof; and (b) a desquamating agent selected from the group consisting of acetyl glucosamine, *Castanea sativa* extract, salicylic acid, lactic acid, glycolic acid, maltobionic acid, gluconolactone, Acacia Senegal gum, *Salix alba* bark extract, yeast extract, glucono-heptono lactone, D-mannose-6-phosphate, polylysine, mushroom extract, galactoarabinan, sodium cholesterol sulfate, N-lactoyl phytosphingosine, forskolin, *Coleus barbatus* extract, phytic acid, cysteamine lactate, mandelic acid, hydroxylauric acid, and mixtures thereof; and (c) a mattifying agent that reduces sebum production in skin cells and/or absorbs sebum produced by skin cells selected from the group consisting of a silicone elastomer, *Serenoa serrulata* extract, NDGA, and mixtures thereof; and (d) an agent that increases skin luminosity selected from the group consisting of silica, fluorescent glass, polyvinylalcohol crosspolymer, fluorescent brighteners, disodium distyrylbenzene sulfonate, polydodecaamideaminium triazadiphenylethenesulfate, HDI/PPG/polycaprolactone crosspolymer mica, boron nitride, nylon, and mixtures thereof wherein the composition containing combined amounts of ingredients (a)-(d) is effective to moisturize, desquamate, mattify, and improve skin luminosity in an individual in need thereof.

2. The method of claim 1 wherein the moisturizing agent acts by replenishing ceramide on the skin surface.

3. The method of claim 1 wherein the moisturizing agent acts by enhancing ceramide production in skin cells.

4. The method of claim 1 wherein the desquamating agent is acetyl glucosamine.

5. The method of claim 1 wherein the mattifying agent reduces sebum production in skin cells.

6. The method of claim 5 wherein the mattifying agent is a silicone elastomer.

7. The method of claim 1 wherein the moisturizing agent is *Rosmarinus officinalis* extract, rosmarinic acid, ursolic acid, or mixtures thereof.

8. The method of claim 1 wherein the desquamating agent is acetyl glucosamine, *Castanea sativa* extract, salicylic acid, *Salix alba* extract or mixtures thereof.

9. The method of claim 1 wherein the mattifying agent is a *Serenoa serrulata* extract.

10. The method of claim 1 wherein the agent that increases skin luminosity is silica, mica, boron nitride, nylon, or mixtures thereof.

11. The method of claim 1 wherein the moisturizing agent is wheat germ extract, barley extract, *Rosmarinus officianalis* extract, or mixtures thereof; the mattifying agent is *Serenoa serrulata* extract; the desquamating agent is *Castenea sativa* or *Salix alba* extract; and the luminosity increasing agent is HDI/PPG/polycaprolactone crosspolymer.

\* \* \* \* \*